United States Patent [19]

Branemark et al.

[11] Patent Number: 4,838,891
[45] Date of Patent: Jun. 13, 1989

[54] JOINT PROTHESIS

[76] Inventors: Per-Ingvar Brånemark, Ändergaten 3, S-431 39 Mölndal; Björn Albrektsson, Rödhakevägen 1, S-430 Kullavik, both of Sweden

[21] Appl. No.: 229,756

[22] Filed: Aug. 8, 1988

Related U.S. Application Data

[63] Continuation of Ser. No. 801,705, Nov. 26, 1985, abandoned.

[30] Foreign Application Priority Data

Nov. 28, 1984 [SE] Sweden ............................ 8405989

[51] Int. Cl.⁴ .............................................. A61F 2/38
[52] U.S. Cl. ................................................... 623/20
[58] Field of Search ................................ 623/20–23

[56] References Cited

U.S. PATENT DOCUMENTS

| | | | |
|---|---|---|---|
| 3,521,302 | 7/1970 | Muller | 623/23 |
| 4,259,072 | 3/1981 | Hirabayashi et al. | 623/23 |
| 4,330,891 | 5/1982 | Branemark | 623/16 |
| 4,353,136 | 10/1982 | Polyzades | 623/20 |
| 4,479,271 | 10/1984 | Bolesky et al. | 623/20 |

FOREIGN PATENT DOCUMENTS

| | | |
|---|---|---|
| 926552 | 5/1973 | Canada . |
| 3417923 | 11/1985 | Fed. Rep. of Germany . |
| 3429157 | 2/1986 | Fed. Rep. of Germany . |
| 2266492 | 10/1975 | France . |
| 2330337 | 6/1977 | France . |
| 2378505 | 8/1978 | France . |
| 2478462 | 9/1981 | France . |
| 2045083 | 10/1980 | United Kingdom . |

Primary Examiner—Vincent Millin
Assistant Examiner—James Prizant
Attorney, Agent, or Firm—Pollock, Vande Sande & Priddy

[57] ABSTRACT

This invention relates to a joint prosthesis for permanent anchorage in the bone tissue of a joint in a human body, for instance a knee joint. The joint prosthesis comprises an anchorage device (3, 4; 7-10, 11) disposed to be implanted into the bone tissue at a first operation so that it remains in unloaded condition during a healing phase during which the function of the joint is not prevented and an articulation device (5, 6; 13, 12) which is arranged to be connected to the anchorage device only at a second operation after the said healing phase.

10 Claims, 9 Drawing Sheets

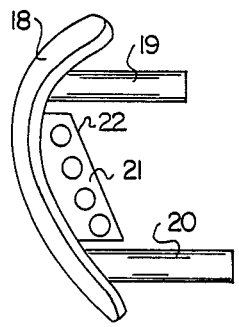
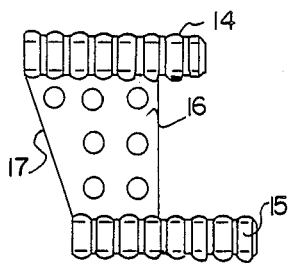
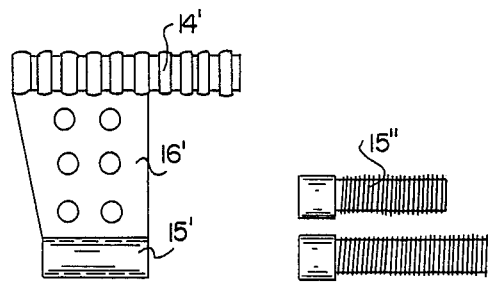
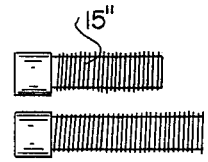
FIG. 4   FIG. 3a   FIG. 3b   FIG. 3c
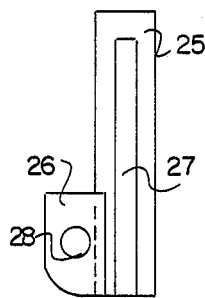
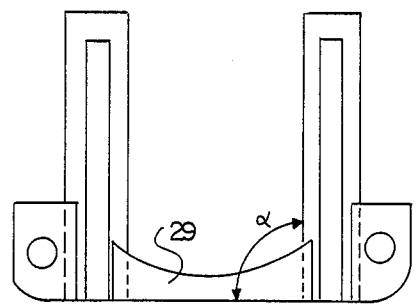
FIG. 6a   FIG. 6b
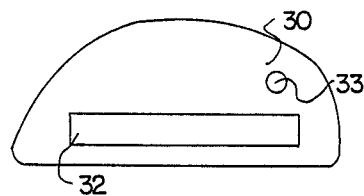
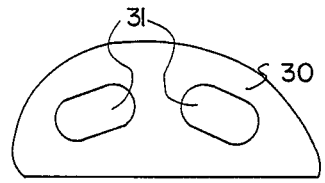
FIG. 7a   FIG. 7b

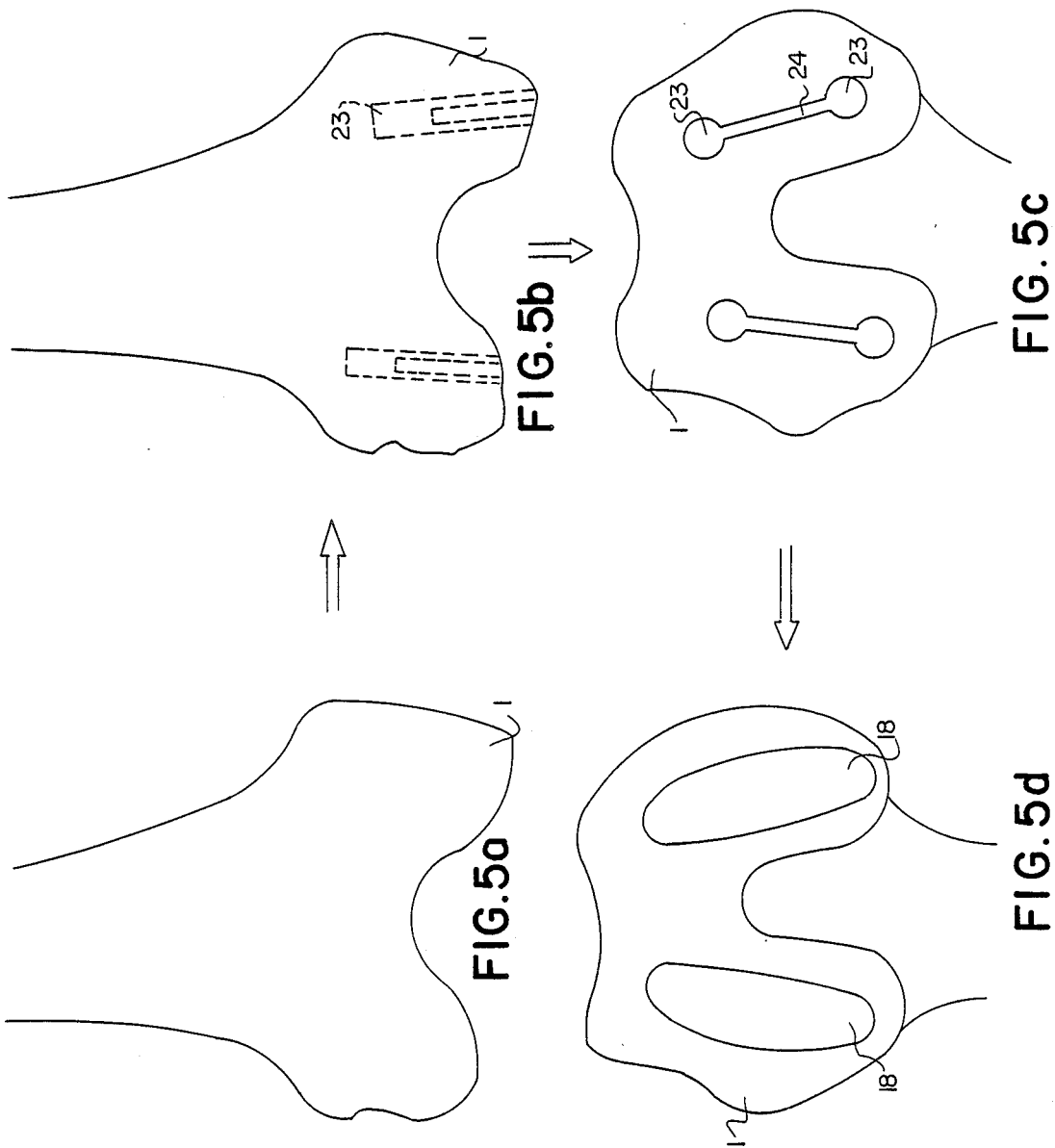

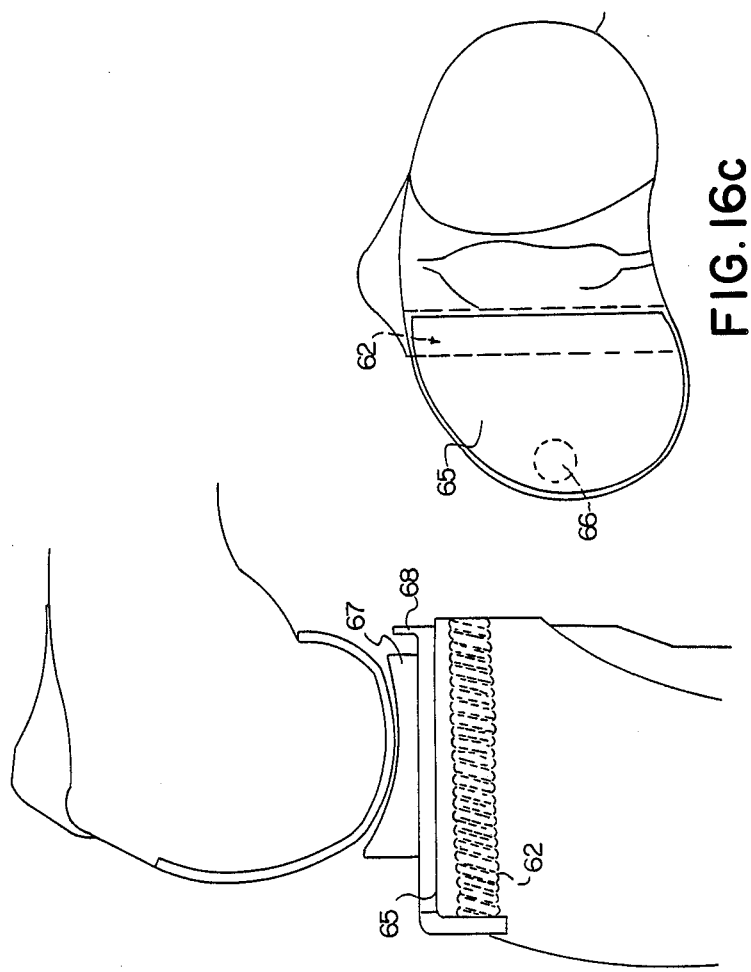

JOINT PROTHESIS

This application is a continuation of Ser. No. 801,705, filed on Nov. 26, 1985, now abandoned.

BACKGROUND OF THE INVENTION

This invention relates to a joint prosthesis for permanent anchorage in the bone tissue of a joint in the human body, for instance a knee joint.

Various methods are already known for dealing with knee joint destruction and other joint diseases or malformations in joints in the human body through prosthetic surgical intervention.

The joints which have been objects of such prosthetic surgical intervention are primarily the knee joint, hip joint, elbow joint, shoulder joint, foot joint and finger joint. The present invention is not confined to any one these joints but will hereinafter be described mainly in conjunction with knee joints, since it is there that there is a pronounced need to extend the indication range for knee joint replacement so that considerably younger patients than at the present time could be offered a solution to their knee problems.

The disease-caused defects concerned are rheumatic knee joint diseases and wear injuries that in the first instance affect joint cartilage and in the second instance underlaying bone tissue which is worn away and gives rise to a varying degree of joint defect. A defect of this nature may be localized and affect only one or two of the three compartments of the knee joint as in the majority of cases of knee joint wear, but it may also be generalized as in rheumatic disease, when both the medical and the lateral knee joint compartments and also the femuro-patellar joint are involved in the same destructive process. In localized knee joint destruction, if the destruction is limited solely to the medial or lateral knee joint compartment, only this part is provided with a prosthesis, in which case it is customery to speak of a demiprosthetic procedure (half-joint prosthesis). If two or three compartments are involved in the arthrosis, it will usually be a matter of a total prosthesis. This is almost always the case with rheumatic diseases.

The disease-caused defect found in connection with a joint-destroying disease or wear injury is often extended in conjunction with prosthetic surgery to make room for the prosthesis and to create a mechanical lock between prosthesis and bone. The contour of the skeleton end is thus removed to fit more or less exactly into the for example multicornered box formed by the surrounding prosthesis. The surgical defect thus encroaches upon intact joint skelton.

The need of stabilization between the parts of the prosthesis varies from one defect situation to another. If the joint ligament apparatus is defective it is prior art knowledge to provide the opposed articulating joint replacements with a coupling in the form of a hinge or piston mechanism which replaces the stabilization normally obtained through ligaments and cruciate ligaments. Such stabilized prostheses are however rather voluminous and increase the surgical defect.

In the majority of cases, around 90 percent of all knee joint destructions, the ligaments and cruciate ligaments are nevertheless so intact that no stabilized prosthesis is needed. All the same, for a moderate but not grave ligament injury some type of retention between the parts of the prosthesis may be necessary and can then be built into the prosthesis design. For example it is known in the art to cup the articulation socket of the prosthesis and to adapt the joint head thereto. A prosthesis of this type is designated as constrained. In a constrained prosthesis there is a good congruence between joint surfaces, implying good stability and less compression stress per unit of area but also increased friction between the joint surfaces and less possibility of movement in certain planes, e.g. translation. A constrained prosthesis retards movements and thus gives rise to strains in mobility planes that are not permitted by the prosthesis and this implies that the prosthesis absorbs constrained forces. This strain will be transmitted to the transition between prosthesis and bone. Experince shows that constrained prostheses have a very high loosening frequency which probably is due to the absorption of constrained forces which are thus transmitted to the transition between prosthesis and bone.

Although a constrained prosthesis can be made less voluminous than the stabilized prosthesis the disadvantage of the high loosening probability nevertheless remains. in recent times, therefore, a new type of prosthesis has been developed, namely a semi-constrained or non-constrained prosthesis. These prostheses have a surface geometry which in principle is characterised by a rounded joint ball which rests against a relatively flat joint socket. These types of prosthesis obviously impose rather high demands on the ligaments and cruciate ligaments for their stabilization but in recompense the ligaments and musculature absorb the strain to which the prosthesis is subjected in all motional planes and the prosthesis will thus not brake the strain on account of its structure so that the constrained forces acting on the transition between prosthesis and bone will be reduced. The frequency of loosening is also significantly lower with this type of prosthesis than with the earlier type, but today the follow-up time for semi-constrained and non-constrained prostheses is far too short to permit any definite conclusions to be reached with regard to the long-term forecast for loosening frequency. One thing, however, is perfectly clear with regard to this type of prosthesis and that is that the contact surface between the parts of the prosthesis is reduced which leads to a greater load with compression forces per unit of area, which involves a risk of mechanical wear. In addition, exacting demands are imposed on the ligaments since the prosthesis is very little stabilized in its own structure.

In summary, it may therefore be said that a constrained prosthesis is exposed to a greater risk of loosening than a non-constrained prosthesis, but the risk of loosening is by no means excluded in that the prosthesis is non-constrained. Moreover, there is a greater risk of mechanical wear problems with non-constrained prostheses.

The problem of mechanical wear has naturally also been studied. On the basis 15 years of clinical experience quite a lot is known about the behaviour of metals, plastics and ceramics as joint replacement materials. Tests have been performed on replacement of both joint socket and joint head with the same material. Different material combination possibilities have also been tried. Steel against steel, for example, has been found to be unfavourable, whereas ceramic against ceramic has proved to be a favourable combination in view of resistance to mechanical wear. This latter combination, however, appears to be advantageous only in ball-and-socket joints. Generally, metal against polyethylene is considered to be an acceptable combination, and it is probable that this particular combination will remain in the forefront of interest for at least another ten years. Polyethylene is biologically inert and has a beneficial elastic deformation that dampens peak forces. Polyethylene is also highly resistant to permanent deformation if the component has a thickness of at least 6 mm and if it is metal-supported in relation to the bone surface. The issue being discussed today therefore is not whether or not the joint surface of the tibial component in a knee joint shall consist of polyethylene but is rather a matter of which metal should be combined with the polyethylene as replacement material for the joint surface of the high bone end. No really certain alternative is, however, afforded here. Further studies of mechanical wear resistance, corrosion resistance, toxic effect etc. are required.

Attempts have been made in various ways to increase the anchorage stability of the joint substitute in the bone tissue. More than twenty years of experience has now been gained of cement fixation (with methyl acrylate) of joint replacements, particularly in hip joints, and it is known that the forecast in the 10-year perspective is reasonable as regards clinical stability of prostheses inserted under optimal conditions. With a greater space of time after the reconstruction the risk of loosening nevertheless increases significantly and this can also be discerned at a relatively early stage. Radiological loosening, in fact, precedes the clinical loosening and can occasionally be seen several years before typical loosening discomfort is experienced by the patient. In view of the doubtful prognosis for cement-fixed prostheses in the long term one is generally undisposed to use such replacements in young patients who not only can be expected to need the prosthesis for a very long time but also subject the bone-prosthesis relation to greater strain on account of a higher level of activity.

It is known in the also art to anchor joint replacements without cement. Freeman introduced his technique for cementless fixation of knee prostheses in 1976 and since the other designs such as PCA, Laskin, N.J., the Galante prosthesis and others have been presented. It is still all too early to arrive at any conclusions about the results of effects to fix knee joint replacements without bone cement but one may nevertheless assert that there is very little evidence to support lasting unchanged stabilization of the above types of prosthesis to underlying bone. All the signs indicate that most, if not all, of the types of prosthesis mentioned hereinbefore appear to be connective tissue-anchored, i.e. surrounded by connective tissue that separates the prosthesis from the bone tissue. A connective tissue zone this nature tends to grow under continued load. This leads to loosening. With regard to the occurrence of such a connective tissue zone, reference may be made to an article by Gerald A Lord et al, "An Uncemented Total Hip Replacement", Clinical Orthopaedics and Related Research No. 141, June 1979.

From the above it is evident that there are several artificial knee joints on the market, but none of these has been shown to establish a long-lasting stable anchorage to the host skeleton.

SUMMARY OF THE INVENTION

An object of the present invention is therefore to provide an improved joint prosthesis giving a solution to several of the problems mentioned hereinbefore and particularly to the problem of fixation.

A further object of the present invention is to be able to reduce the surgical defect upon prosthetic surgery, i.e. to reduce the removal of intact bone tissue during the operation.

Yet a further object of the invention is to be able to extend the indication range, especially for knee prosthetic surgery and to provide a joint replacement material that permits the introduction of artificial knee joints among far younger patients than at the present time.

Further objects of the invention will become apparent from the following description.

The present invention is thus based on the osseointegration principle as previously described by Brånemark and his colleagues with regard to jaw-bone anchored dental bridges. The only implant that hitherto has been demonstrated to remain anchored via direct contact between bone and implant, osseointegration, is in fact Brånemark's jaw bone anchored dental bridge. The anchorage of these dental bridges is based on the cornerstones of atraumatic insertion technique, anchorage portions of commercially pure titanium, unloaded healing phase of critical length and secondary operation with connection of load portions. The invention is then characterized largely in that an anchorage device is arranged to be implanted in the bone tissue at a first operation. This unloaded device heals in during a healing period without disturbing the function of the adjacent joint. In a second operation an articulation device is connected to the anchorage device which has become incorporated in the host skeleton.

A joint prosthesis of this kind then normally comprises two parts, namely one for each of the two opposite articulating bone ends in a joint, for instance a femoral component and a tibial component in a knee joint. In an advantageous embodiment of the present invention each of the parts of the prosthesis comprises such an anchorage device plus a connected articulation device. The articulation devices are then adapted to each other to permit the wanted freedom of movement between the bone ends.

The actual articulation devices may have a slightly different design depending on the joint concerned. One part of the prosthesis may be provided with a fixed articulation device of metal with a rounded, more or less anatomically correct articulatory surface as that of the normal femoral condyle while the other adjacent articulatory surface device may consist of a polyethylene component fixed or movably disposed on a metal socket which in turn is connected to the anchorage device of the other part of the prosthesis (for instance the tibial component).

In an advantageous embodiment at least the anchorage devices are made of commercially pure titanium.

Some advantageous embodiments of the invention in conjunction with knee joint will be described in greater detail below.

Through this invention the unreliability of fixation found in earlier designs of knee prostheses can be eliminated. The invention provides a metal-to-bone-anchorage of the repalaement and in this respect the invention represents a radically new approach. A two-phase surgical operation is a prerequisite for lasting anchorage. It also provides an interval for "tailoring" the articulation device to fit in exactly at the host site which can be three-dimensionally defined during the first operation by means of a casting procedure. This combination of operation technique and prosthesis design is completely unique. The invention also offers the advantage that no gross removal of healthy bone has to be performed to create a mechanical interlock between the reshaped skeletal end and the multicornered interior surface of a conventional prosthesis. Instead only small amounts of bone have to be removed to replace the joint surfaces with the technique describrd above. A decisive advantage with the invention is that it affords a possibility for retained skeleton fixation for a long time, which implies that it should be possible to increase the indication range for example for knee joint replacement so that considerably younger patients than at present can be offered this type of solution to their severe knee problems. At the present time, considerable doubts are entertained about inserting knee prostheses in patients less than 60 years of age. Through the solution of the fixation problems provided by the present invention there is justification for the hope that the indication range will be extended to also include patients less than 60 years of age.

BRIEF DESCRIPTION OF THE DRAWINGS

In the following the invention will now be described in more detail with reference to the accompanying drawings, in which FIG. 3 illustrates two examples of anchorage devices for the femur, FIG. 4 illustrates a corresponding articulation surface device for the femur, FIG. 5 illustrates schematically a two-phase surgical procedure applied to the femoral component, FIG. 6 illustrates an anchorage device for the tibia in a unicondylar (6a) and bicondylar (6b) version, FIG. 7 illustrates a corresponding articulation device for the tibia, FIG. 15 illustrates a tibia component with an anchorage device as well as an articulation device and FIG. 16 illustrates a further embodiment of the tibia component.

DESCRIPTION OF THE PREFERRED EMBODIMENTS

Figure 1A:
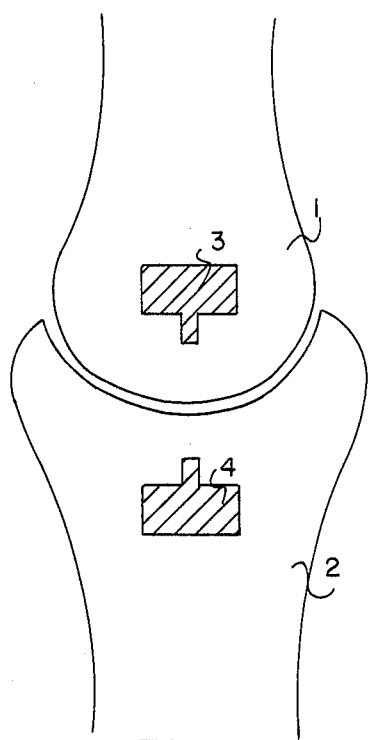
FIG. 1 illustrates schematically a first embodiment of the present invention.
Figure 1B:
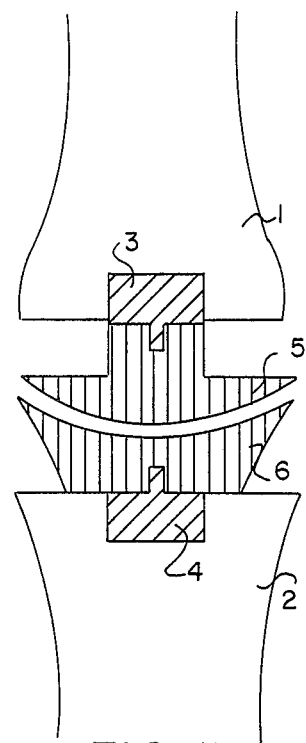
Figure 2A:
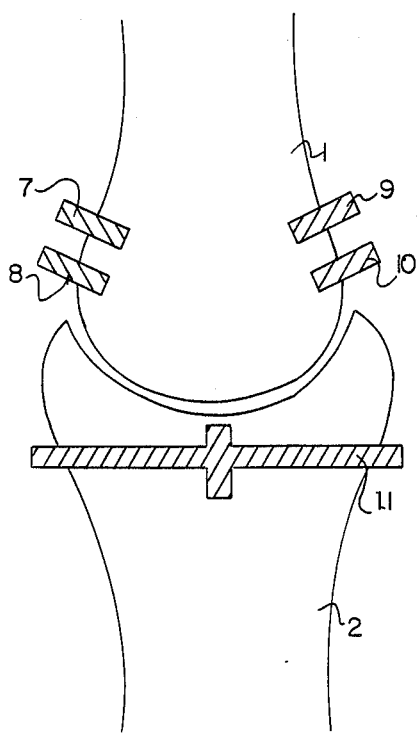
FIG. 2 illustrates schematically an alternative embodiment.

FIGS. 1 and 2 thus illustrate schematically the main principle of the present invention for a general joint in the human body. In conjunction with FIGS. 3–16, a more detailed description is then given of how the anchorage and articulation devices can be designed in the knee joint prosthesis. FIGS. 3–11 illustrate a first embodiment and FIGS. 12–16 a second, preferred embodiment. Even though the invention is now described essentially in conjunction with a knee joint it will nevertheless be realized that it is by no means confined to this joint.

As evident from the above summary, the invention is based on the establishment of a permanent anchorage between the bone tissue in the joint and the prosthesis. To permit such a permanent anchorage, so-called osseointegration, certain factors must be satisfied, namely atraumatic insertion techique, anchorage devices in a special "tissue-compatible" material such as commercially pure titanium, an unloaded healing phase of critical length and a secondary operation with connection of the desired replacement portion, i.e. a two-phase surgical procedure with an interlying unloaded healing period.

Also mentioned in the introduction the osseointegration principle has been previously described in connection with jaw-bone anchored dental bridges, see e.g.

P-I Brånemark et al "Osseointegrated titanium fixtures in the treatment of edentulousness", Biomaterials, 1983, Vol 4, January and Richard Skalak "Biomechanical Considerations in osseointegrated prostheses", The Journal of prosthetic Dentist, June 1983, Volume 49, Number 6.

This technique has been used clinically with excellent results for 20 years and in the following description it will be illustrated how the technique can be applied to anchorage of joint replacements.

Illustrated in FIG. 1 is a joint, for instance a knee joint with a femur 1 (thigh bone end) and tibia 2 (shin bone end), which is assumed to have a disease-caused defect which requires a joint replacement prosthesis. A prosthesis of this kind must then comprise partly a femoral component and partly a tibial component with opposed articulating surfaces. To permit permanent anchorage in the bone tissue both the femoral and the tibial component are built up of two devices, partly an anchorage device 3, 4 and partly an articulation device 5, 6. These two devices are disposed to be operated into the leg in a two-phase surgical procedure, the anchorage devices 3, 4 at the first operation, FIG. 1a, while the articulation device, 5, 6, are first connected at a second operation after a healing phase, see FIG. 1a.

The implantation of the anchorage devices 3, 4 is performed in such a manner that the prerequisites for osseointegration are satisfied (see above). This technique is, as evident from the above, in itself already known and will therefore not be described more closely here. What is new, however, for the present invention is that the anchorage devices are implanted in a different type of bone tissue than previously, namely not in the flat bone of the facial skeleton as in the jaw-joint) but instead in tubular bone, and that the devices are adapted to the specific requirements which must be satisfied in a joint. Typical of the invention is that the anchorage devices are implanted in such a manner that the defective joint surface is left entirely or almost entirely intact at this first operation, i.e. the surgical defect is limited to only what is required for implantation of the anchorage devices. The patient remains mobile during the healing phase which is a condition for a functional joint. The invention is the only known design which satisfies this requirement. The anchorage device can thus be operated in from the side, from the front or from the joint surface itself. In the latter case, it is true that the joint surface is interfered with, but this damage is so limited that it does not appreciably deteriorate the function of the joint during the healing phase. It is also the latter case that is illustrated more in detail in conjunction with FIGS. 3-8 and 12-14, respectively, below for the femoral component. As the articulation portions are not connected during the healing phase it will be realized that the anchorage devices are not subjected to load during this phase.

First during a second operation, which is carried out roughly 3-4 months after the first one, are the articulation portions coupled to the tibia and femur. During this procedure bone has to be removed to make room for the articulatory surface replacements. The condition after this second operation is illustrated schematically in FIG. 1b.

Figure 2B:
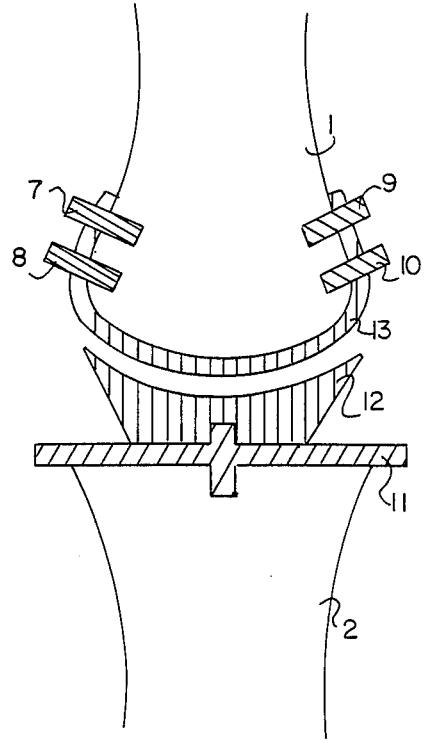

Illustrated schematically in FIG. 2 is a somewhat different elaboration of the joint prosthesis. The anchorage portion of the femoral component consists in this case of a plurality of separate fixtures 7, 8 and 9, 10, which are operated in from the side during the first phase. These fixtures may nevertheless be advantageously connected together in pairs. The anchorage device of the tibial component is envisaged to consist of a through-going cylindrical fixture 11 with means for connection of articulation portion 12, see FIG. 2b. The replaced articular surfaces fit well to the cut bone surfaces due to the possibility of "tailoring" the articulating components between the two operations. In this case the surgical removal of healthy bone tissue in the femoral end will be minimal.

Illuatrated in FIG. 3 are two examples of anchorage devices for the femur, which are intended to be inserted from the joint surface. The anchorage device according to FIG. 3a consists of two parallel, tube-shaped fixture legs 14, 15 with an external rifling which forms the healing surface against the bone tisue. The two fixture legs are interconnected by means of a holed plate 16 so that the anchorage device forms a so-called twin fixture or "double barrel". The anchorage device may comprise a further development of the fixtures developed by P-I Brånemark for dental bridges, but has been adapted to the specific requirements which must be satisfied for a knee joint. In this case the fixture legs are interconnected and unable to move relative to each other and the stability increases. The interconnection portion 16 is also so elaborated that the healing surface towards the bone tissue increases. The portion 16 also forms a supporting surface 17 which rests against a corresponding surface of the articulation device and helps to absorb compression forces. The anchorage device is made of commercially pure titanium with an oxidized surface and a surface structure which is previously known in the connection with jaw-bone fixtures. See for example Swedish Pat. No. 79.02035-0.

The anchorage device according to FIG. 3b also consists of two parallel, tube-shape fixture legs 14', 15' of which one has an external rifling which forms a healing surface against the bone tissue. The fixture legs are interconnected by means of a holed plate 16' so that the anchorage device also in this embodiment forms a so-called twin-fixture. In contrast to the embodiment described in FIG. 3a one fixture leg 15' is substantially shorter and the anchorage in this case is accomplished by means of a separate fixture screw 15" (FIG. 3c) which is screwed into fixture leg 15' which for this purpose is provided with an internal thread. The fixture screw 15" is tube-shaped and smooth-drilled internally in the same way as fixture legs 14 and 15 in FIG. 3a to fit the articulation device. (see below).

The advantage of this embodiment which thus exploits a fixture screw similar to those previously used for dental bridges is that the fixture screw 15" can be made in several different lengths, two of which are illustrated in FIG. 3c, and that the anchorage device thus becomes more flexible.

Illustrated in FIG. 4 is how the articulation device for the femoral component is designed. The articulation device consists of an articulatory surface rail 18 to which two connection rods 19, 20 have been welded. The articulatory surface rail is anatomically designed and may have three different sizes for each femoral condyle. The articulation portion consists of commercially pure titanium, possibly with an articulatory surface layer of some other, wear-resistant material. The articulation device is also provided with a holed, plate-shaped portion 21 to increase the healing surface. The portion 21 also has a contact surface 22 which corresponds to the supporting surface 17 of the anchorage device.

The connection rods 19, 20 are adapted for insertion in the fixture legs 14, 15 of the anchorage device upon connection of the articulation device at the second operation. In contrast to the jaw-bone fixtures, the articulation device is not screwed on but is fitted into the anchorage device. The desired degree of stiffness for fitting of the articulation device is accomplished with slightly tapered and/or angled connection rods 19, 20. In contrast to jaw fixtures, there will be no tensile forces so that the locking is fully sufficient.

In conjunction with FIGS. 3 and 4 the design of the femoral component with anchorage device and articulation device according to a first embodiment has now been shown. Illustrated in FIG. 5 is how the two-phase surgical procedure is applied to the femoral component. FIG. 5a shows the end contour of the femur viewed from the front and it is assumed that both femoral condyles have a defect which requires joint replacement. In FIG. 5b and 5c, the femur is illustrated from the front and from the joint surface after the first operation with an anchorage device implanted into each femoral condyle. The limited surgical defect in the form of two drill holes 23 for the fixture legs 14, 15 and a narrower recess 24 for the connection plate 16 resulting from the first operation is clearly evident from FIG. 5c. Only at the second operation phase surgical, when the articulation device is connected, see FIG. 5d, is some removal of the end contour of the femur carried out for adaptation of the articulatory surface rails.

Illustrated in FIG. 6 is an example of anchorage devices for the tibia, partly a unicondylar (6a) and a bicondylar version (6b), and which is arranged to be inserted from the front. The unicondylar anchorage device consists of an extended cylindrical rod 25 fitted with a side portion 26. The upper surface of the rod 25 is planed off and provided with an anchorage mechanism in the form of a dove-tailed recess 27 which extends along the planed-off side of the rod facing towards the surface of the joint and which is to permit connection from the front of the articulation device of the tibia. The side portion 26 is also provided with an anchoring mechanism in the form of the screw hole 28 for locking of the articulation device. The bycondylar anchorage device, see FIG. 6b, consists of two rod-shaped anchorage portions which are interconnected with a disk-shaped portion 29. It is also evident from FIG. 6b that the angle between the anchorage portion and the interconnection portion 29 slightly exceeds 90° which is occasioned by the contour of the tibial condyles.

The anchorage device for the tibia is also made of commercially pure titanium and arranged to be implanted in the tibia in a first operation so that an osseointegration takes place. Only after a healing phase of 3-4 months is/are the articulation device or devices for the tibia connected. Here, the devices differ from one another medially and laterally since an artificial meniscus is inserted on the medial side in the joint for improved congruence. Laterally, there is no meniscus, the articulation device then being provided with an anchorage mechanism for a soild polyethylene component with a slightly dished tibial condyle which leads directly to a round femoral condyle. Laterally, the joint is thus non-constrained.

The medial articulation device is illustrated in FIG. 7 and consists in principle of a segment-shaped metal socket 30 the upper surface of which is ground smooth and has a running groove in the form of two guide tracks 31 for steering of the artificial meniscus, FIG. 7b, and its lower surface, which faces towards the anchorage device, is also flat but has a connection piece in the form of a dove-tailed rail 32 adapted to the recess 27 in the anchorage device and a screw hole 33 adapted to the hole 28 in the side portion of the anchorage device, see FIG. 7a. In the same way as the other devices, the articulation device of the tibia is preferably made of commercially pure titanium.

In conjunction with FIGS. 6 and 7 the constructed design of the tibial component with its anchorage device and articulation device has now been illustrated. Shown in FIGS. 8 and 9 is how the two-phase surgical procedure is applied to the tibia component both unicondylarly and bicondylarly.

Figure 8B:
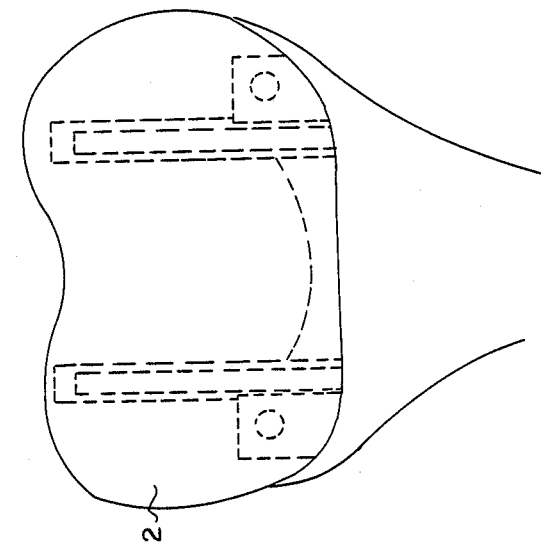
FIG. 8 illustrates schematically phase 1 in a two-phase surgical procedure applied to the tibial component.
Figure 8D:
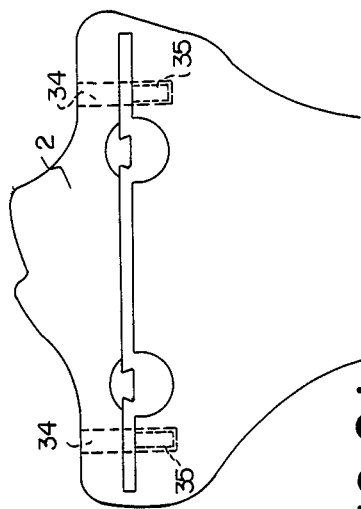
Figure 8A:
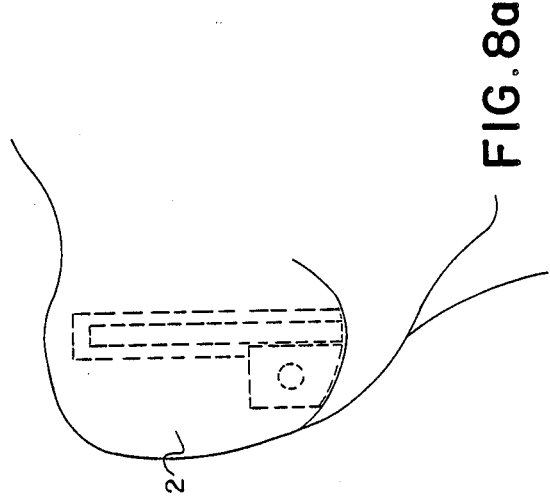
Figure 8C:
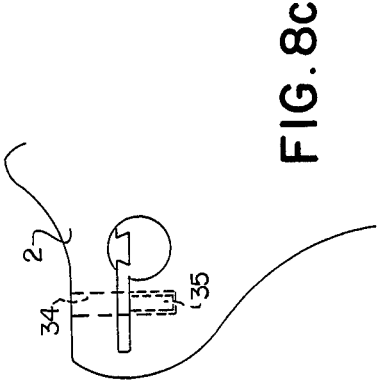
Figure 9B:
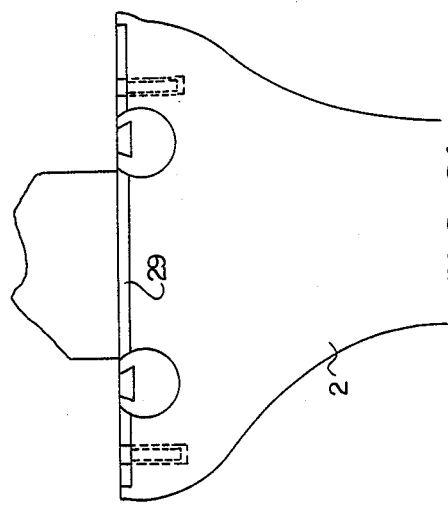
FIG. 9 illustrates schematically phase 2 in a two-phase surgical procedure applied to the tibial component.
Figure 9D:
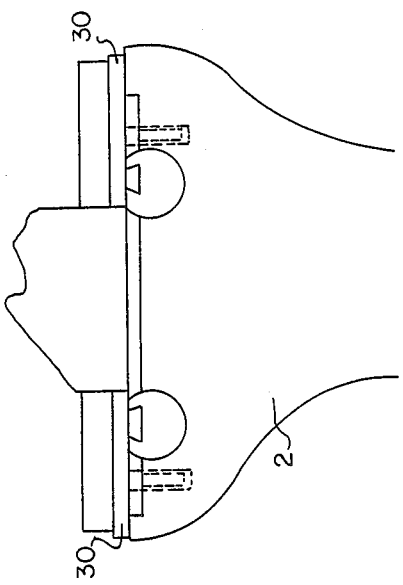
Figure 9A:
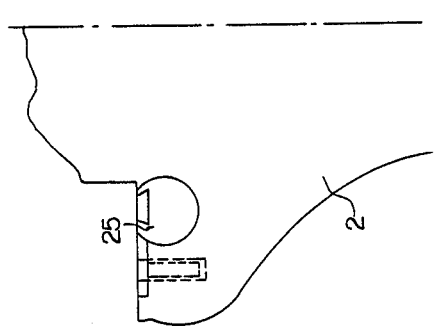
Figure 9C:
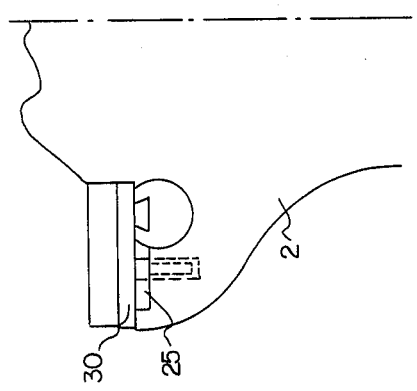
Figure 10A:
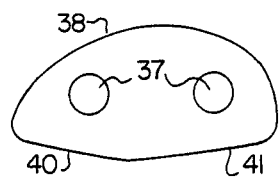
FIG. 10 illustrates an artificial meniscus for connection of the articulation portion of the tibial component.
Figure 10B:
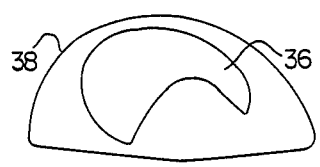

FIG. 8 then shows the condition after the first operation with the anchorage devices inserted, seen partly from the articulation surface (FIG. 8a and 8b) and partly from the front (FIG. 8c and 8d). Here too, the surgical defect is, as may be seen, very limited and the articualtion surfaces of the tibia are completely intact apart from the recess 34 for a fixture 35 which is connected to the side portion 24 of the anchorage device.

Shown in FIG. 9 is the condition after the second operation, the end contour of the tibia being shown from the front after surgical removal of the end contour of the tibia which is necessary to make room for the articulation device replacement in the form of a metal socket and meniscus medially and of a flat non-mobile tibial bearing component of polyethlene laterally.

Figure 11A:
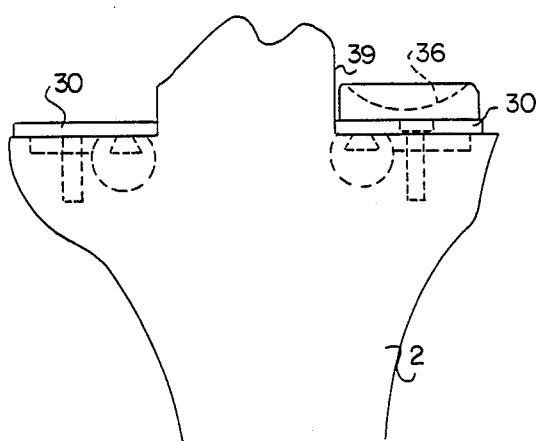
FIG. 11 illustrates schematically from the front and from the articulation surface the tibial component complete with connected meniscus medially.
Figure 11B:
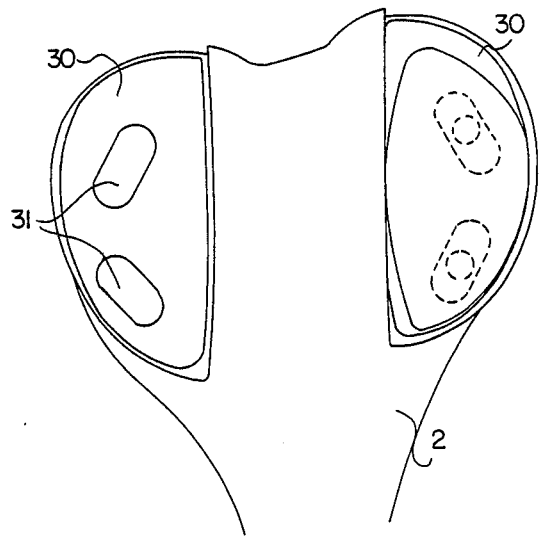

Illustrated in FIG. 11 is the complete tibial component with connected meniscus medially in a view partly from the front (FIG. 11a) and partly from the articulatory surface (FIG. 11b). As evident from FIG. 11b the outer contours of both the socket 30 and the meniscus agree with the end contour of the removed tibial condyle. The meniscus is nevertheless smaller so that it is able to move unobstructedly over the socket 30.

Figure 12:
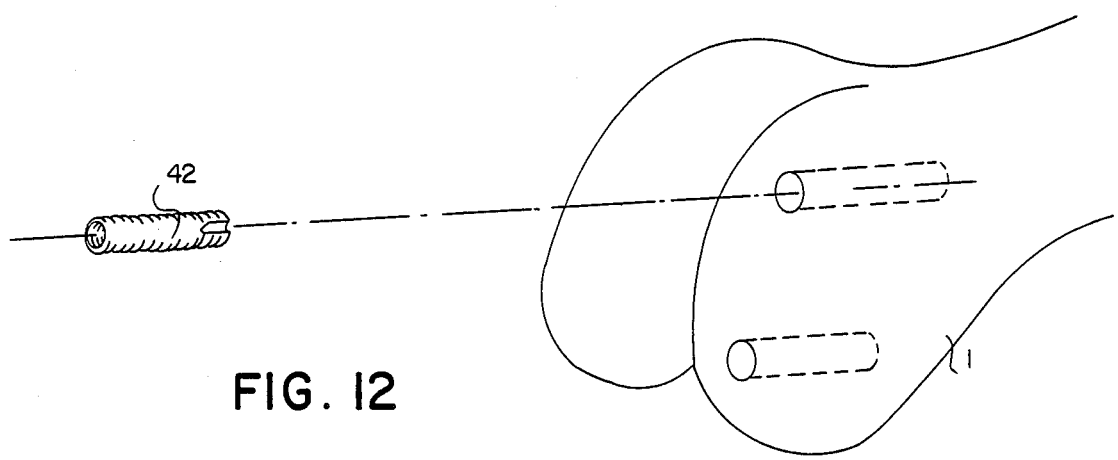
FIG. 12 illustrates another preferred embodiment of anchorage device for the femur.

In the following a second, preferred embodiment will be described with reference to FIGS. 12–16. Illustrated in FIG. 12 is an anchorage device for the femur which consists of titanium fixture screws 42 separately anchored into the bone tissue through an external screw thread. The fixtures are a further development of the fixtures developed by P-I Brånemark for dental bridges, but has been adapted to the specific requirements which must be satisfied for a knee joint. For reliable anchorage of the articulation device at least two fixture screws will usually be required, to which the articulation device will subsequently be connected. The placing of the fixtures is done very accurately with the aid of aligning instruments.

The fixture screws 42 are made of commercially pure titanium like the twin fixtures of FIG. 3. The fixture screws are tublar with an external thread which forms a healing surface against the bone-tissue and an internal thread for connecting the articulation device.

Figure 13:
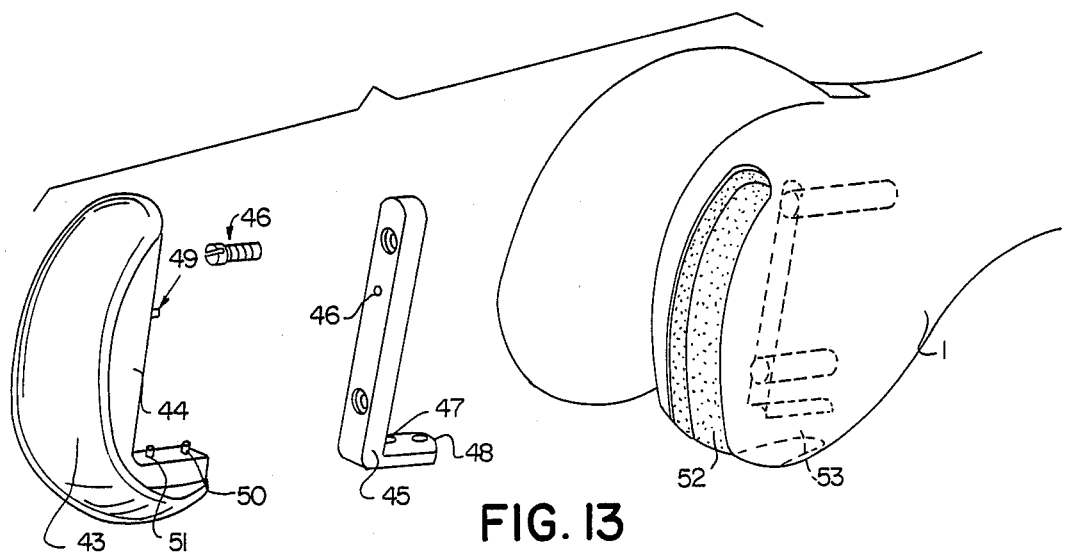
FIG. 13 illustrates a corresponding articulation device for the femur.

FIG. 13 illustrates the corresponding articulation device for the femoral component, which in this case consists of two separate parts, an articulatory surface rail part 43, which has an L-shaped socket 44, and an interconnecting L-shaped element 45. Like the articulation device 18, 19, 20 illustrated in FIG. 4, in this case also the articulatory surface rail is anatomically designed and consists of commercially pure titanium. The interconnecting element 45 is connected to the fixture screws 42 by means of two locking screws 46 which are screwed into the tubular fixtures 42. The interconnecting elements 45 has three further holes for locking the articulatory surface rail part 43, one hole 46 which is parallel to the fixture screws and two holes 47, 48 on the shorter angled part of the element which holes are perpendicular to the fixture screws. The articulatory surface socket 44 has corresponding guiding pins 49, 50, 51 for securing the articulation device in a plane parallel to the fixture screws as well as in a perpendicular plane. One of the guiding pins 50, 51 on the shorter angled socket part conical and the guiding pin 49 is spring actuated for locking the articulatory surface rail part 43 to the interconnecting element 45.

In this embodiment the two-phase surgical procedure is also applied to the femoral component. In a first operation the fixture screws 42 are implanted into one or each of the femoral condyles. In this operation there is only a limited surgical defect in the form of two drill holes. Only at the second operation, after the healing phase, is a removal 52 of the end contour of the femur carried out for adaption of the interconnecting element 45, see FIG. 13. The removal is effectuated by means of the fixture screws as references and is carried out down to the fixture screw ends so that there is a plane perpendicular to the fixtures. There is also a removal 53 in a perpendicular plane at the back of the femoral condyle to provide a base for the L-shaped interconnecting element 45. The width of the removal is adapted to the width of the socket 44 of the articulatory surface rail part.

Figure 14:
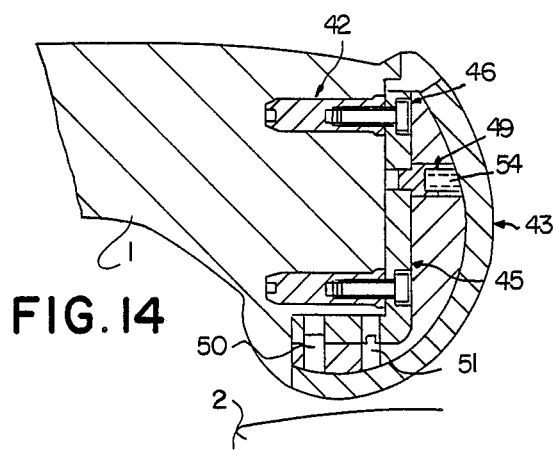
FIG. 14 illustrates the assembled femoral prosthesis component.

FIG. 14 is a section through an assembled femoral component illustrating the different parts, specifically also the guiding pin 49 actuated by means of a spring 54. The femoral component is entirely secured to the femur and can be removed only by destructing the articulatory surface.

Figure 15C:
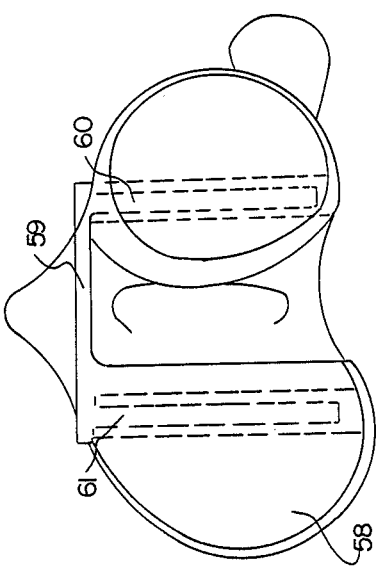
Figure 15B:
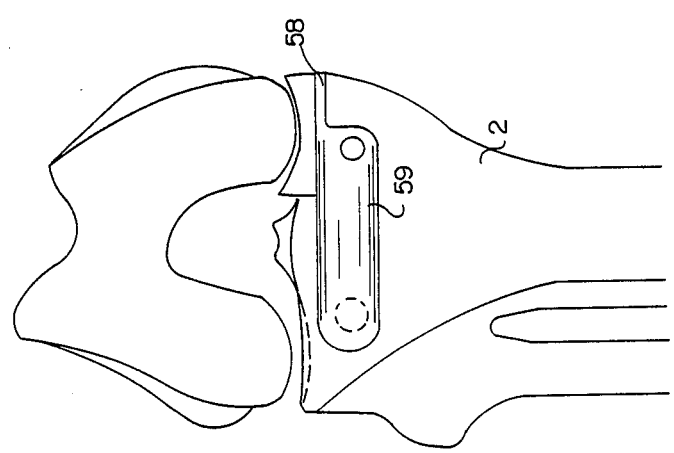
Figure 15A:
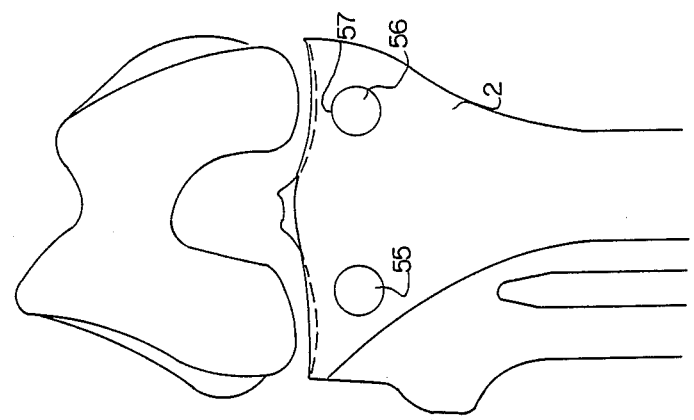

Illustrated in FIG. 15 is also a further embodiment of the tibia component based on two titanium fixture screws, one lateral 55 and one medial 56, as an anchorage device. The fixture screws are inserted from the front in a first operation so that an osseointegration takes place, see FIG. 15a. After a healing phase of 3–4 months the articulation device for the tibia is connected to the two titanium screws after a surgical removal of the end contour of the tibia to make room for the articulation device.

Like the fixture screws in the femur, the tibial fixture screws 55 and 56 are also made of commercially pure titanium. The screws are tubular with an external thread which forms a healinng surface against the bone-tissue. The screws are smooth-drilled internally and provided with a longitudinal slit 57 for the connnection of the tibia articulation device.

A medial, unicondylar articulation device is illustrated in FIG. 15b, seen from the front, and in FIG. 15c, seen from the articulation surface. The articulation device is connected to the titanium fixture screws and comprises a medial segment-shaped metal socket 58, one cross-beam 59 and two solid, cylindrical guiding rods 60, 61 inserted into the fixture screws. The articulation device is made as a single unit, perferably of commercially pure titanium. The medial guiding rod 61 is connected to the lower surface of the socket 58 by means of a longitudinal beam extending through the slit 57 in the titanium screw 56. Any torsional moment on the medial tibia socket 58 is compensated by the lateral fixture screw 55 via said cross beam 59.

FIGS. 15b and c illustrate a unicondylar version. It should be understood, however, that a bicondylar version is based on the same principle. In this case there is a medial as well as a lateral segment-shaped metal socket connected by a cross-beam. Each of the sockets are then connected to its guiding rod through a longitudinal, vertical beam extending through the fixture screw slit.

FIG. 16 illustrated in different views a modified, unicondylar tibia component which is also based on titanium fixture screws as an anchorage device. In this case a tubular fixture screw 62, like screw 56, is inserted form the front in the first operation so that an osseointegration takes place. Only after the healing phase of 3–4 months there is a surgical removal of the end contour of the tibia to make room for the articulation device in the form of a flat metal socket 65 provided with a cylindrical, solid rod 63 connected to the socket via a longitudinal, vertical beam 64.

The fixture screw 62 is used as an aligning reference during the surgical removal. The end contour of the tibia is removed to such an extent that there is a certain pretension between the socket 65 and the underlying bone tissue surface. As in this case there in only one transverse fixture screw 62 it might be necessary to provide the socket with an additional, peripheral vertical screw 66 inserted in the second operation to compensate for any torsional moment.

The metal socket 65 is provided with an artificial meniscus 67 of polyethylene movably disposed on the plane upper surface of the tibia metal socket. The magnitude of the movement backwards is limited by a posterior edge 68 on the socket as illustrated in FIG. 16b.

The invention is not limited to the embodiments described above but can be varied within the scope of the accompanying claims.

We claim:

1. A joint prosthesis for permanent anchorage in bone tissue of a joint in a human body, for example, a knee joint, comprising:

at least two anchorage devices, at least one of them for implantation into bone tissue of each of the femoral and tibial components, respectively, during a first surgical operation, each of said anchorage devices including at least one fixture leg forming a healing surface towards surrounding bone tissue during a healing phase, said anchorage device remaining in an unloaded condition during said healing to allow functioning of the joint;

at least two articulation devices, at least one of them for each of the femoral and tibial components, respectively, each articulation device including a corresponding articulatory surface and connecting means for interconnecting said articulation device to said firmly anchored fixture leg during a second operation subsequent to said healing phase, wherein at least said anchorage devices are made of pure titanium; and, wherein said anchorage device for the femoral component comprises at least two separate internally threaded tubular members forming said leg fixtures insertable from the femur joint surface and said articulation device for the femoral component further comprises an articulatory surface rail part and a separate interconnecting L-shape part connected to said tubular members by two locking screws screwed into threaded interior of said tubular members.

2. A joint prosthesis according to claim 1 wherein said fixture leg comprises a tubular member having an external threaded surface, said external threaded surface forming said healing surface contacting said surrounding bone tissue.

3. A joint prosthesis according to claim 2 wherein said tubular member has a threaded interior for receiving said connecting means for connecting said articulation device.

4. A joint prosthesis accorididng to claim 1 wherein said articulatory surface rail part includes an L-shaped socket conforming to said interconnecting element and means for securing said articulation device both in the parallel and perpendicular plane to said tubular fixture members.

5. A joint prosthesis according to claim 4 wherein said anchorage device for the tibial component comprises at least one fixture member insertable from the front in the tibia and said articulation device for the tibial component comprises a medial and/or lateral shaped metal socket and at least one cylindrical guiding road connected to said socket through a vertical beam.

6. A joint prosthesis according to claim 5 wherein said articulation device for the tibial component comprises a cross beam and two solid cylindrical guiding roads insertable into said tibial fixture members.

7. A joint prosthesis according to claim 5 wherein said fixture members are provided with a longitudinal sleeve through which said vertical beam of said articulation device is extending when said articulation device is connected to said fixture member in the second operation subsequent to said healing phase.

8. A joint prosthesis according to claim 5 wherein said medial tibial metal socket is provided with an artificial menisus of polyethylene movably disposed on the plane upper surface of said socket and a posterior edge to limit the magnitude of the movement of the meniscus backwardly.

9. A joint prosthesis for permanent anchorage in bone tissue of a joint in a human body, for example, a knee joint, comprising:

at least two anchorage devices, at least one of them for implantation into bone tissue of each of the femoral and tibial components, respectively, during a first surgical operation, each of said anchorage devices including at least one fixture leg forming a healing surface towards surrounding bone tissue and adapted to be firmly anchored into said tissue during a healing phase, said anchorage device remaining in an unloaded condition during said healing phase to allow functioning of the joint, and;

at least two articulation devices, at least one of them for each of the femoral and tibial components, respectively, each articulation device including a corresponding articulatory surface and connecting means for interconnecting said articulation device to said firmly anchored fixture leg during a second operation subsequent to said healing phase, wherein at least said anchorage devices are made of pure titanium; and, wherein said anchorage device for the femoral component comprises at least two separate screw-shaped tubular members forming said leg fixtures and screwable in the bone tissue and said articulation device for the femoral compnent further comprises an articulatory surface part and a separate L-shaped interconnecting part connected to said tubular members.

10. A joint prosthesis according to claim 9, wherein said articulatory surface part includes an L-shaped socket conforming to said interconnecting part and means for securing said articulation device both in the parallel and perpendicular plane to said tubular fixture members.

* * * * *